(12) United States Patent
Tsujimoto et al.

(10) Patent No.: US 7,211,421 B2
(45) Date of Patent: May 1, 2007

(54) **GENE ENCODING DIHYDRODIPICOLINATE REDUCTASE FROM *BACILLUS METHANOLICUS***

(75) Inventors: Nobuharu Tsujimoto, Kawasaki (JP); Hisashi Yasueda, Kawasaki (JP); Yoshio Kawahara, Kawasaki (JP); Shinichi Sugimoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 23 days.

(21) Appl. No.: 11/073,741

(22) Filed: Mar. 8, 2005

(65) Prior Publication Data
US 2005/0233416 A1  Oct. 20, 2005

Related U.S. Application Data

(62) Division of application No. 10/214,556, filed on Aug. 9, 2002, now Pat. No. 6,878,533, which is a division of application No. 09/631,828, filed on Aug. 3, 2000, now Pat. No. 6,461,852.

(30) Foreign Application Priority Data
Aug. 4, 1999  (JP) ................................ 11-221468

(51) Int. Cl.
*C12N 9/02* (2006.01)
*C12P 13/08* (2006.01)

(52) U.S. Cl. ...................... 435/189; 435/115
(58) Field of Classification Search ................ None
See application file for complete search history.

(56) References Cited

U.S. PATENT DOCUMENTS

| | | | |
|---|---|---|---|
| 4,346,170 A | 8/1982 | Sano et al. | |
| 5,426,052 A | 6/1995 | Flickinger et al. | |
| 6,110,713 A | 8/2000 | Hanson et al. ............. | 435/110 |
| 6,461,852 B1 | 10/2002 | Tsujimoto et al. | |
| 2002/0155556 A1 | 10/2002 | Imaizumi et al. | |
| 2002/0160461 A1 | 10/2002 | Nakai et al. | |
| 2003/0013174 A1 | 1/2003 | Tsujimoto et al. | |
| 2003/0049805 A1 | 3/2003 | Nagase et al. | |
| 2003/0077764 A1 | 4/2003 | Tsujimoto et al. | |
| 2003/0124687 A1 | 7/2003 | Gunji et al. | |
| 2003/0166174 A1 | 9/2003 | Ono et al. | |
| 2003/0232338 A1 | 12/2003 | Usuda et al. | |
| 2004/0142435 A1 | 7/2004 | Gunji et al. | |
| 2004/0146974 A1 | 7/2004 | Gunji et al. | |
| 2004/0166570 A1 | 8/2004 | Yasueda et al. | |
| 2004/0170985 A1 | 9/2004 | Usuda et al. | |
| 2004/0170986 A1 | 9/2004 | Usuda et al. | |
| 2004/0170987 A1 | 9/2004 | Usuda et al. | |
| 2004/0171134 A1 | 9/2004 | Yasueda et al. | |
| 2004/0191875 A1 | 9/2004 | Takeshita et al. | |
| 2004/0197918 A1 | 10/2004 | Matsuzaki et al. | |
| 2004/0214296 A1 | 10/2004 | Asahara et al. | |
| 2004/0229305 A1 | 11/2004 | Usuda et al. | |
| 2004/0229311 A1 | 11/2004 | Hirano et al. | |
| 2005/0003495 A1 | 1/2005 | Gunji et al. | |

FOREIGN PATENT DOCUMENTS

| | | |
|---|---|---|
| EP | 0 841 395 | 5/1998 |
| KR | 92-8382 | 9/1992 |
| WO | WO 96/40934 | 12/1996 |
| WO | WO 99/20783 | 4/1999 |

OTHER PUBLICATIONS

Kunst et al. (1997) Nature, The complete genome sequence of the Gram-positive bacterium *Bacillus subtilis*, vol. 390, pp. 249-256.*
Sorokin et al. (1996) Microbiology, Sequence analysis of the *Bacillus subtilis* chromosome region between the serA and kdg loci cloned in a yeast artificial chromosome, vol. 142, pp. 2005-2016.*
N. Y. Chen, et al., Database SWAL 'Online ACQ04796, pp. 1-2, "Dihydrodipicolinate Synthase (EC 4.2.1.52) (DHDPS)(Vegetative Protein 81)" Oct. 1, 1993.
A. V. Sorokin, et al., Database SWAL 'Online AC P42976, 1 Page, "Dihydrodipicolinate Reductase (EC 1.3.1.26) (DHRP)" Nov. 1, 1995.
L. Eggeling, et al., Applied Microbiology and Biotechnology, vol. 49, No. 1, pp. 24-30, "Improved L-Lysine Yield With Corynebacterium Glutamicum; Use of dapA Resulting in Increased Flux Combined With Growth Limitation", 1998.
D. A. Mills, et al., "Cloning and Sequencing Analysis of the Meso-Diaminopimelate Decarboxylase Gene From *Bacillus methanolicus* MGA3 and Comparison to Other Decarboxylase Genes", Applied and Environmental Microbiology, Sep. 1993, vol. 59, No. 9, pp. 2927-2937.
F. J. Shendel, et al., "Cloning and Nucleotide Sequence of Gene Coding for Aspartokinase II From a Thermophilic Methylotrophic *Bacillus* Sp", Applied and Environmental Microbiology, Sep. 1992, vol. 58, No. 9, pp. 2806-2814.
G. H. Lee, et al., "Lysine Production From Methanol at 50° C Using *Bacillus methanolicus* Medeling Volume Control, Lysine Concentration, and Productivity Using a Three-Phase Continuous Simulation", Biotechnology and Bioengineering, Oct. 4, 1996, vol. 49, pp. 639-653.

(Continued)

*Primary Examiner*—Kathleen M. Kerr
*Assistant Examiner*—Alexander Kim
(74) *Attorney, Agent, or Firm*—Cermak & Kenealy, LLP; Shelly Guest Cermak

(57) ABSTRACT

An *Escherichia coli* mutant strain deficient in dihydrodipicolinate synthase or dihydrodipicolinate reductase is transformed with a chromosomal gene library of *Bacillus methanolicus,* and a transformant strain which can grow on a minimal medium is selected. Recombinant DNA which codes for dihydrodipicolinate synthase or dihydrodipicolinate reductase (named dapB) is obtained from the transformant.

12 Claims, No Drawings

OTHER PUBLICATIONS

GenBank Accession No. L08471. *Bacillus subtillis*, 3' end, dipicolinate synthase subunits A and B, aspartate semialdehyde dehydrogenase, aspartokinase, dihydropicolinate synthase (dapA) genes (1993).

Shevchenko et al., "Expression of the genes for lysine biosynthesis of *Bacillus subtilis* in *Escherichia coli*", Tsitol Genet., 1984, vol. 18, No. 1, pp. 58-60.

J. Bouvier, et al., "Nucleotide Sequence and Expression of the *Escherichia coli* DAPB Gene", The Journal of Biological Chemistry, Dec. 10, 1984, vol. 259, No. 23, pp. 14829-14834.

B. Dauce-Le Reverend, et al., "Improvement of *Escherichia coli* Strains Overproducing Lysine Using Recombinant DNA Techniques", European Journal of Applied Microbiology and Biotechnology, 1982, vol. 15, pp. 227-231.

A. Pisabarro, et al., "A Cluster of Three Genes (dapA, orf2, and dapB) of Brevibacterium Lactofermentum Encodes Dihydrodipicolinate Synthase. Dihydrodipicolinate Reductase, and a Third Polypeptide of Unknown Function", Journal of Bacteriology, May 1993, vol. 175, No. 9, pp. 2743-2749.

GenBank Accession No. E46665. dihydrodipicolinate synthase (EC4.2.1.52) dapA[similarity]-*Bacillus subtilis*. Created May 3, 1994.

Pavelka Jr., M. S., et al., "Cloning to the *dapB* Gene, Encoding Dihydrodipicolinate Reductase, from *Mycobacterium tuberculosis*," J. Bacteriol. 1997;179(8):2777-2782.

European Search Report for EP Patent Appl. No. 05017544.7 (Dec. 13, 2005).

* cited by examiner

SEQUENCE LISTING

```
<160> NUMBER OF SEQ ID NOS: 4

<210> SEQ ID NO 1
<211> LENGTH: 873
<212> TYPE: DNA
<213> ORGANISM: Bacillus methanolicus
<220> FEATURE:
<221> NAME/KEY: CDS
<222> LOCATION: (1)..(870)

<400> SEQUENCE: 1 atg gtt tct ttt ggt cga ata tca aca gct atg gtt aca cca ttt gat        48
Met Val Ser Phe Gly Arg Ile Ser Thr Ala Met Val Thr Pro Phe Asp
1               5                   10                  15 aac aaa ggt cat att gat ttt gca aaa aca acg caa ctc gtg aat cat        96
Asn Lys Gly His Ile Asp Phe Ala Lys Thr Thr Gln Leu Val Asn His
                20                  25                  30 tta att aat aat ggt tca gat tct tta gtt gtt gtc ggt act act gga       144
Leu Ile Asn Asn Gly Ser Asp Ser Leu Val Val Val Gly Thr Thr Gly
            35                  40                  45 gag tca gcc aca ctt aca aaa gaa gaa aaa ttg gcg ctt ttt cag cat       192
Glu Ser Ala Thr Leu Thr Lys Glu Glu Lys Leu Ala Leu Phe Gln His
        50                  55                  60 gta gta aaa gta gtt gaa aaa aga gtc cct gtt att gca ggc acc gga       240
Val Val Lys Val Val Glu Lys Arg Val Pro Val Ile Ala Gly Thr Gly
65                  70                  75                  80 agc aat aat act tat gat tca atc gaa atg aca aaa aaa gca gaa aaa       288
Ser Asn Asn Thr Tyr Asp Ser Ile Glu Met Thr Lys Lys Ala Glu Lys
                85                  90                  95 atg ggc gtc gat gcg att ttg gca gtt gct ccg tat tat aac aaa cca       336
Met Gly Val Asp Ala Ile Leu Ala Val Ala Pro Tyr Tyr Asn Lys Pro
                100                 105                 110 aac cag gaa gga tta tat caa cat ttt aag gca att gct gaa agt aca       384
Asn Gln Glu Gly Leu Tyr Gln His Phe Lys Ala Ile Ala Glu Ser Thr
            115                 120                 125 tcc ctt cct gtt atc att tat aac att ccc gga aga tct gtt gtg aat       432
```

| | | |
|---|---|---|
| Ser Leu Pro Val Ile Ile Tyr Asn Ile Pro Gly Arg Ser Val Val Asn<br>    130                 135                 140 | | |
| atc gag cct gaa acg gtc atc cgt ttg tcc aag att ccg aac att gtt<br>Ile Glu Pro Glu Thr Val Ile Arg Leu Ser Lys Ile Pro Asn Ile Val<br>145                 150                 155                 160 | | 480 |
| ggt atc aaa gaa gca ggc ggg aat ctt agt gcg atg acg caa att att<br>Gly Ile Lys Glu Ala Gly Gly Asn Leu Ser Ala Met Thr Gln Ile Ile<br>                    165                 170                 175 | | 528 |
| gcc aat aca gat gac gat ttt ctt ttg tat agc gga gac gac ggt tta<br>Ala Asn Thr Asp Asp Asp Phe Leu Leu Tyr Ser Gly Asp Asp Gly Leu<br>                180                 185                 190 | | 576 |
| acc ttg cca gta ctg tcc att ggc gga acc ggg gtt att tct gtg gca<br>Thr Leu Pro Val Leu Ser Ile Gly Gly Thr Gly Val Ile Ser Val Ala<br>            195                 200                 205 | | 624 |
| tcc cat gtt atc gga aat gaa atg caa gaa atg atc agt gca ttt tta<br>Ser His Val Ile Gly Asn Glu Met Gln Glu Met Ile Ser Ala Phe Leu<br>        210                 215                 220 | | 672 |
| aat gga gat tat gaa cgt gcg gca aaa att cat caa aag ctg ctt ccg<br>Asn Gly Asp Tyr Glu Arg Ala Ala Lys Ile His Gln Lys Leu Leu Pro<br>225                 230                 235                 240 | | 720 |
| ctt atg gat gga tta ttt atc gct cca aac cct gta ccg gtt aaa act<br>Leu Met Asp Gly Leu Phe Ile Ala Pro Asn Pro Val Pro Val Lys Thr<br>                    245                 250                 255 | | 768 |
| gct ttg caa att aaa ggc atg gat gtc ggt tcg gtt cgc ttg cct ctt<br>Ala Leu Gln Ile Lys Gly Met Asp Val Gly Ser Val Arg Leu Pro Leu<br>                260                 265                 270 | | 816 |
| gtt ccg ctt act gaa caa gag cga aat aca gtg gca gca tta tta aat<br>Val Pro Leu Thr Glu Gln Glu Arg Asn Thr Val Ala Ala Leu Leu Asn<br>            275                 280                 285 | | 864 |
| gct tta taa<br>Ala Leu<br>    290 | | 873 |

<210> SEQ ID NO 2
<211> LENGTH: 290
<212> TYPE: PRT
<213> ORGANISM: Bacillus methanolicus

<400> SEQUENCE: 2

Met Val Ser Phe Gly Arg Ile Ser Thr Ala Met Val Thr Pro Phe Asp
1               5                   10                  15

Asn Lys Gly His Ile Asp Phe Ala Lys Thr Thr Gln Leu Val Asn His
            20                  25                  30

Leu Ile Asn Asn Gly Ser Asp Ser Leu Val Val Gly Thr Thr Gly
        35                  40                  45

Glu Ser Ala Thr Leu Thr Lys Glu Glu Lys Leu Ala Leu Phe Gln His
    50                  55                  60

Val Val Lys Val Val Glu Lys Arg Val Pro Val Ile Ala Gly Thr Gly
65                  70                  75                  80

Ser Asn Asn Thr Tyr Asp Ser Ile Glu Met Thr Lys Lys Ala Glu Lys
                85                  90                  95

Met Gly Val Asp Ala Ile Leu Ala Val Ala Pro Tyr Tyr Asn Lys Pro
            100                 105                 110

Asn Gln Glu Gly Leu Tyr Gln His Phe Lys Ala Ile Ala Glu Ser Thr
        115                 120                 125

Ser Leu Pro Val Ile Ile Tyr Asn Ile Pro Gly Arg Ser Val Val Asn
    130                 135                 140

Ile Glu Pro Glu Thr Val Ile Arg Leu Ser Lys Ile Pro Asn Ile Val

-continued

```
                    145                 150                 155                 160
        Gly Ile Lys Glu Ala Gly Gly Asn Leu Ser Ala Met Thr Gln Ile Ile
                        165                 170                 175

Ala Asn Thr Asp Asp Asp Phe Leu Leu Tyr Ser Gly Asp Asp Gly Leu
                    180                 185                 190

Thr Leu Pro Val Leu Ser Ile Gly Thr Gly Val Ile Ser Val Ala
                    195                 200                 205

Ser His Val Ile Gly Asn Glu Met Gln Glu Met Ile Ser Ala Phe Leu
                    210                 215                 220

Asn Gly Asp Tyr Glu Arg Ala Ala Lys Ile His Gln Lys Leu Leu Pro
        225                 230                 235                 240

Leu Met Asp Gly Leu Phe Ile Ala Pro Asn Pro Val Pro Val Lys Thr
                        245                 250                 255

Ala Leu Gln Ile Lys Gly Met Asp Val Gly Ser Val Arg Leu Pro Leu
                        260                 265                 270

Val Pro Leu Thr Glu Gln Glu Arg Asn Thr Val Ala Ala Leu Leu Asn
                    275                 280                 285

Ala Leu
            290
```

<210> SEQ ID NO 3
<211> LENGTH: 801
<212> TYPE: DNA
<213> ORGANISM: Bacillus methanolicus
<220> FEATURE:
<221> NAME/KEY: CDS
<222> LOCATION: (1)..(798)

<400> SEQUENCE: 3

```
atg gaa att gta aaa att gtt gta gca ggc ccg cgc gga cga atg ggg      48
Met Glu Ile Val Lys Ile Val Val Ala Gly Pro Arg Gly Arg Met Gly
1               5                   10                  15 cgg gaa gca gtc cat ctt gtc ggg aga aca gaa aat ttc gag ttg gca      96
Arg Glu Ala Val His Leu Val Gly Arg Thr Glu Asn Phe Glu Leu Ala
            20                  25                  30 gca gtg ctg gat aat aag aat gac gga aaa aat ctt tcc gaa ttg gaa     144
Ala Val Leu Asp Asn Lys Asn Asp Gly Lys Asn Leu Ser Glu Leu Glu
        35                  40                  45 ggt ttt caa gga ttt gat gcc cct gtg tat aca aat att gaa aaa tgt     192
Gly Phe Gln Gly Phe Asp Ala Pro Val Tyr Thr Asn Ile Glu Lys Cys
    50                  55                  60 ttt caa gat acc ggc gca gat gtc tta atc gat ttg acg act cct gaa     240
Phe Gln Asp Thr Gly Ala Asp Val Leu Ile Asp Leu Thr Thr Pro Glu
65                  70                  75                  80 gta ggc tac tat cat aca aaa acg gct ctc gaa tat gga gtg cgg cct     288
Val Gly Tyr Tyr His Thr Lys Thr Ala Leu Glu Tyr Gly Val Arg Pro
                85                  90                  95 gta gtt ggg acg acg ggt ttt acg aaa gat caa tta aaa gaa att gaa     336
Val Val Gly Thr Thr Gly Phe Thr Lys Asp Gln Leu Lys Glu Ile Glu
            100                 105                 110 gaa att tgc gaa gaa aag aaa ctt ggc tgc att ata gcg cca aat ttt     384
Glu Ile Cys Glu Glu Lys Lys Leu Gly Cys Ile Ile Ala Pro Asn Phe
        115                 120                 125 gcg gtt ggg gct gta tta atg atg aaa ttt tca caa atg gca gcc aag     432
Ala Val Gly Ala Val Leu Met Met Lys Phe Ser Gln Met Ala Ala Lys
    130                 135                 140 tat ttt caa gat att gaa att att gaa ctg cat cat gat caa aaa ttg     480
Tyr Phe Gln Asp Ile Glu Ile Ile Glu Leu His His Asp Gln Lys Leu
145                 150                 155                 160
```

```
gat gca ccg tcc gga aca gct gtc aaa aca gct gag atg att gcg gaa    528
Asp Ala Pro Ser Gly Thr Ala Val Lys Thr Ala Glu Met Ile Ala Glu
            165                 170                 175 gtg aga gaa gca aag aag cag ggt cat cca aat gaa aaa gaa acg atc    576
Val Arg Glu Ala Lys Lys Gln Gly His Pro Asn Glu Lys Glu Thr Ile
        180                 185                 190 atc ggt gca agg ggt gcg gat tat gaa gga atg cat att cat tct gtt    624
Ile Gly Ala Arg Gly Ala Asp Tyr Glu Gly Met His Ile His Ser Val
    195                 200                 205 cgt ttg ccg gga tta att gcc cat cag cag gtg atg ttt gga tca gac    672
Arg Leu Pro Gly Leu Ile Ala His Gln Gln Val Met Phe Gly Ser Asp
210                 215                 220 ggg caa aca ttg acg atc cgc cac gat tcg tat aac cgg gca tct ttc    720
Gly Gln Thr Leu Thr Ile Arg His Asp Ser Tyr Asn Arg Ala Ser Phe
225                 230                 235                 240 atg tct ggc gta aag cat gcc gtt gag acg gtt tta aaa att gat acg    768
Met Ser Gly Val Lys His Ala Val Glu Thr Val Leu Lys Ile Asp Thr
                245                 250                 255 ttt gtt tac gga tta gaa aat att att gaa tag                        801
Phe Val Tyr Gly Leu Glu Asn Ile Ile Glu
            260                 265

<210> SEQ ID NO 4
<211> LENGTH: 266
<212> TYPE: PRT
<213> ORGANISM: Bacillus methanolicus

<400> SEQUENCE: 4

Met Glu Ile Val Lys Ile Val Val Ala Gly Pro Arg Gly Arg Met Gly
1               5                   10                  15

Arg Glu Ala Val His Leu Val Gly Arg Thr Glu Asn Phe Glu Leu Ala
            20                  25                  30

Ala Val Leu Asp Asn Lys Asn Asp Gly Lys Asn Leu Ser Glu Leu Glu
        35                  40                  45

Gly Phe Gln Gly Phe Asp Ala Pro Val Tyr Thr Asn Ile Glu Lys Cys
    50                  55                  60

Phe Gln Asp Thr Gly Ala Asp Val Leu Ile Asp Leu Thr Thr Pro Glu
65                  70                  75                  80

Val Gly Tyr Tyr His Thr Lys Thr Ala Leu Glu Tyr Gly Val Arg Pro
                85                  90                  95

Val Val Gly Thr Thr Gly Phe Thr Lys Asp Gln Leu Lys Glu Ile Glu
            100                 105                 110

Glu Ile Cys Glu Glu Lys Lys Leu Gly Cys Ile Ile Ala Pro Asn Phe
        115                 120                 125

Ala Val Gly Ala Val Leu Met Met Lys Phe Ser Gln Met Ala Ala Lys
    130                 135                 140

Tyr Phe Gln Asp Ile Glu Ile Glu Leu His His Asp Gln Lys Leu
145                 150                 155                 160

Asp Ala Pro Ser Gly Thr Ala Val Lys Thr Ala Glu Met Ile Ala Glu
                165                 170                 175

Val Arg Glu Ala Lys Lys Gln Gly His Pro Asn Glu Lys Glu Thr Ile
            180                 185                 190

Ile Gly Ala Arg Gly Ala Asp Tyr Glu Gly Met His Ile His Ser Val
        195                 200                 205

Arg Leu Pro Gly Leu Ile Ala His Gln Gln Val Met Phe Gly Ser Asp
    210                 215                 220
```

-continued

```
Gly Gln Thr Leu Thr Ile Arg His Asp Ser Tyr Asn Arg Ala Ser Phe
225                 230                 235                 240

Met Ser Gly Val Lys His Ala Val Glu Thr Val Leu Lys Ile Asp Thr
                245                 250                 255

Phe Val Tyr Gly Leu Glu Asn Ile Ile Glu
                260             265
```

GENE ENCODING DIHYDRODIPICOLINATE REDUCTASE FROM *BACILLUS METHANOLICUS*

This application claims benefit under 35 U.S.C. §120 as a divisional application of Ser. No. 10/214,556, filed Aug. 9, 2002 now U.S. Pat. No. 6,878,533, which is a divisional of Ser. No. 09/631,828, now U.S. Pat. No. 6,461,852, filed Aug. 3, 2000.

BACKGROUND OF THE INVASION

1. Field of the Invention

The present invention relates to dihydrodipicolinate synthase and dihydrodipicolinate reductase derived from thermophilic *Bacillus* bacteria and genes encoding the same.

2. Brief Description of the Related Art

In the production of L-lysine by fermentation, strains isolated from nature or artificial mutants thereof have been used to improve productivity. Many artificial mutant strains that produce L-lysine are known, and many of them are aminoethylcysteine (AEC) resistant strains and belong to the genus *Brevibacterium, Corynebacterium, Bacillus*, or *Escherichia*. Furthermore, various techniques have been disclosed for increasing amino acid production by such stains, for example, use of a transformant obtained by using recombinant DNA (U.S. Pat. No. 4,278,765).

Dihydrodipicolinate synthase (abbreviated as "DDPS" hereinafter) is an enzyme that synthesizes dihydrodipicolinate through dehydration condensation of aspartic acid semialdehyde and pyruvic acid, and this reaction serves as a starting point of the L-lysine biosynthesis system for the biosynthesis of aspartic acid-type amino acids. Furthermore, dihydrodipicolinate reductase (abbreviated as "DDPR" hereinafter) is known as one of the important enzymes of the Lysine biosynthesis system, and catalyzes the reaction in which the dihydrodipicolinate generated in the aforementioned reaction is reduced to generate piperidinedicarboxylic acid.

As for microorganisms belonging to the genus *Escherichia* or *Corynebacterium*, the gene (dapA) which codes for DDPS has been cloned, and the nucleotide sequence thereof has also been determined. As for the genus *Escherichia*, methods for producing L-lysine by enhancing DDPS have been disclosed in Japanese Patent Laid-open Publication (Kokai) No. 56-18596/1981, U.S. Pat. No. 4,346,170, and Applied Microbiology and Biotechnology, 15, pp. 227–331 (1982). Furthermore, a method for producing L lysine using an *Escherichia* bacterium into which DDPS derived from *Corynebacterium* bacteria has been introduced is known. DDPS derived from *Corynebacterium* is known to not suffer feedback inhibition by L-lysine, and has been disclosed in Korean Patent Publication No. 92-8382.

The gene coding for DDPR (dapB) has also been obtained from the genus *Escherichia* (Bouvier, J. et al., *J. Biol. Chem*, 259, 14829 (1984)) and the genus *Corynebacterium* (*Journal of Bacteriology*, 175(9), 2743–2749(1993)). Furthermore, a method for improving the production rate and production of L-lysine by enhancing the dapB gene derived from *Corynebacterium* bacterium together with the aspartokinase gene (WO96/40934) has been disclosed.

The current maintain of L-lysine production is fermentative production using a coryneform bacterium or an *Escherichia* bacterium. In this production, however, enzymes required for the fermentation may be inactivated or the production bacteria may be killed due to a temperature increase in the medium during the fermentation, and thus it is necessary to cool the medium during the fermentation.

Enzymes and proteins produced by thermophilic bacteria are generally stable at elevated temperatures, and are also stable against pH variation or organic solvents. Therefore, applications thereof as diagnostic regents, industrial catalysts, and so forth have been highly developed. If it is possible to produce L-lysine by fermentation at elevated temperatures by utilizing stable and durable enzymes derived from thermophilic bacteria, cooling of the medium becomes unnecessary and thereby reduces the cost. Moreover, if fermentation at elevated temperatures is realized it is expected that the reaction rate may also be improved

SUMMARY OF THE INVENTION

The present invention is accomplished in view of the aforementioned technical aspect, and the object is to obtain genes of the L-lysine biosynthesis system from thermophilic bacteria and thereby provide novel methods for producing L-lysine.

The inventors of the present invention assiduously studied in order to achieve the aforementioned object. As a result, genes that code for DDPS and DDPR from *Bacillus methanolicus* have been successfully isolated. *Bacillus methanolicus* is a thermophilic *Bacillus* bacteria, and the nucleotide sequences of these genes have been determined. Thus, the present invention has been completed.

That is, the present invention provides the following.

It is an object of the present invention to provide a protein defined in the following (A) or (B): (A) a protein which has the amino acid sequence of SEQ ID NO: 2 shown in Sequence Listing, or (B) a protein which has an amino acid sequence of SEQ ID NO: 2 shown in Sequence Listing including substitution, deletion, insertion, addition or inversion of one or several amino acids, and has dihydrodipicolinate synthase activity.

It is an object of the present invention to provide a DNA which codes for a protein defined in the following (A) or (B): (A) a protein which has the amino acid sequence of SEQ ID NO: 2 shown in Sequence Listing, or (B) a protein which has an amino acid sequence of SEQ ID NO: 2 shown in Sequence Listing including substitution, deletion, insertion, addition or inversion of one or several amino acids, and has dihydrodipicolinate synthase activity.

It is a further object of the present invention to provide the DNA as described above, which is a DNA defined in the following (a) or (b): (a) a DNA which has a nucleotide sequence comprising at least the nucleotide sequence of the nucleotide numbers 1 to 924 in SEQ ID NO: 1 shown in Sequence Listing; or (b) a DNA which is hybridizable with a nucleotide sequence comprising at least the nucleotide sequence of the nucleotide numbers 1 to 924 in SEQ ID NO: 1 shown in Sequence Listing under a stringent condition, and codes for a protein having dihydrodipicolinate synthase activity.

It is a further object of the present invention to provide the DNA as described above, wherein the stringent condition is a condition in which washing is performed at 60° C., 1×SSC and 0.1% SDS.

It is an object of the present invention to provide the a protein defined in the following (C) or (D): (C) a protein which has the amino acid sequence of SEQ ID NO: 4 shown in Sequence Listing, or (D) a protein which has an amino acid sequence of SEQ ID NO: 4 shown in Sequence Listing including substitution, deletion, insertion, addition or inversion of one or several amino acids, and has dihydrodipicolinate reductase activity It is a further object of the present invention to provide a DNA which codes for a protein defined in the following (C) or (D): (C) a protein which has the amino acid sequence of SEQ ID NO: 4 shown in Sequence Listing, or (D) a protein which has an amino acid sequence of SEQ ID NO: 4 shown in Sequence Listing including substitution, deletion, insertion, addition or inversion of one or several amino acids, and has dihydrodipicolinate reductase activity.

It is a further object of the present invention to provide the DNA as described above, which is a DNA defined in the following (c) or (d): (c) a DNA which has a nucleotide sequence comprising at least the nucleotide sequence of the nucleotide numbers 1 to 798 in SEQ ID NO: 3 shown in Sequence Listing; or (d) a DNA which is hybridizable with a nucleotide sequence comprising at least the nucleotide sequence of the nucleotide numbers 1 to 798 in SEQ ID NO: 3 shown in Sequence Listing under a stringent condition, and codes for a protein having dihydrodipicolinate reductase activity.

It is a further object of the present invention to provide the DNA as described above, wherein the stringent condition is a condition in which washing is performed at 60° C., 1×SSC and 0.1% SDS.

It is a further object of the present invention to provide a microorganism which is introduced with the DNA as described above in a form that allows expression of a protein encoded by each DNA.

It is a further object of the present invention to provide a method for producing L-lysine, which comprises culturing the microorganism according to (9) in a medium to produce and accumulate L-lysine in the medium, and collecting the L-lysine from the medium.

According to the present invention, DDPS and DDPR, which are involved in the L-lysine biosynthesis, have excellent heat resistance, are provided, and the genes coding for them.

PREFERRED EMBODIMENTS OF THE INVENTION

Hereinafter, the present invention will be explained in detail.

The DNA of the present invention can be obtained by selecting clones containing a DDPS or a DDPR gene based on the recovery of auxotrophic mutant strains of microorganisms deficient in DDPS or DDPR from a gene library of thermophilic *Bacillus* bacteria, for example, *Bacillus methanolicus*.

In the present invention, the expression of "to have dihydrodipicolinate synthase activity" is used to mean to have an activity for catalyzing the reaction of dehydration condensation of aspartic acid semialdehyde and pyruvic acid to generate dihydrodipicolinate. The expression of "to have dihydrodipicolinate reductase activity" is used to mean to have an activity for catalyzing the reaction of reduction of dihydrodipicolinate to generate piperidinedicarboxylic acid, and to mean that the activity is higher at 50° C. than at 37° C.

The method for obtaining the DNA of the present invention will be explained below.

<1> Production of Gene Library of *Bacillus methanolicus*

A gene library of *Bacillus methanolicus* can be produced, for example, as follows. First, total chromosomal DNA is prepared by the method of Saito et al. (Saito, H. and Miura, K, *Biochem. Biophys. Acta*, 72, 619–629, (1963)) or the like from a wild-type strain of *Bacillus methanolicus*, for example, *Bacillus methanolicus* PB1 (NCIMB13113) strain, and partially digested with a suitable restriction enzyme, for example, Sau3AI and so forth to obtain a mix of various fragments. If the degree of the digestion is controlled by adjusting digestion reaction time and so forth, a wide range of restriction enzymes can be used.

Subsequently, the digested chromosomal DNA fragments are ligated to a DNA vector which is autonomously replicable within *Escherichia coli* cells to produce a recombinant DNA. More specifically, a restriction enzyme producing the same end nucleotide sequence as the restriction enzyme used for the digestion of the chromosomal DNA is allowed to act on the vector DNA to fully digest the vector and cleave it. Then, the mix of the chromosomal DNA fragments and the cleaved vector DNA obtained as described above are mixed, and a DNA ligase, preferably T4 DNA ligase, is allowed to act on the mixture to obtain recombinant DNA.

*Escherichia coli*, for example, the *Escherichia coli* JM109 strain and so forth, is transformed, with the recombinant DNA obtained as described above, and a gene library can be prepared from the culture. The transformation can be performed by, for example, the method of D. M. Morrison (Methods in Enzymology, 68, 326 (1979)), and the method in which recipient cells are treated with calcium chloride so as to increase the permeability of the cells for DNA (Mandel, M and Higa, A., J. Mol. Biol., 53, 159(1970)). Electroporation was employed in the examples mentioned below.

Examples of the vector include, for example, pUC19, pUC18, pBR322, pHSG299, pHSG298, pHSG399, pHSG398, RSF1010, pMW119, pMW118, pMW219, pMW218, pSTV28, and so forth. In addition, phage vectors can also be used For example, since a chloramphenicol resistance gene is contained in pSTV28, only transformants harboring the vector or the recombinant DNA can be grown using a medium containing chloramphenicol.

Examples of the method for collecting recombinant DNA from the cells after the transformants are cultured include the alkali SDS method and so forth.

<2> Screening of Clones Containing the DDPS or DDPR Gene

By using a gene library of *Bacillus* methanlicus obtained as described above, a mutant microorganism strain deficient in DDPS or DDPR is transformed, and clones showing recovery of auxotrophy are selected. Examples of a mutant microorganism strain deficient in DDPS include *Escherichia coli* AT998 (CGSC4548). Since the *Escherichia coli* AT998 stain is deficient in the DDPS gene, it cannot grow in a minimal medium that does not contain diaminopimelate. On the other hand, a transformant strain thereof which harbors the DDPS gene derived from *Bacillus methanolicus* can grow in minimal medium due to the functional gene. Therefore, a DNA fragment containing the DDPS gene can be obtained by selecting a transformant strain that can grow in minimal medium, and collecting the recombinant DNA from the strain.

Examples of a mutant microorganism stain deficient in DDPR include the *Escherichia coli* AT999 strain (CGSC 4549). Since the *Escherichia coli* AT999 strain is deficient in the DDPR gene, it growth rate is slow, even in a complete medium such as L medium if it does not contain diaminopimelate. On the other hand, a transformant strain thereof which harbors the DDPR gene derived from *Bacillus methanolicus* shows normal growth due to the functional gene. Furthermore, the *Escherichia coli* AT999 cannot grow in a minimal medium, whereas a transformant strain thereof which harbors the DDPR gene derived from *Bacillus methanolicus* can grow in minimal medium due to the functional gene. Therefore, a DNA fragment containing the DDPR gene can be obtained by selecting a transformant strain which can grow in minimal medium, and collecting the recombinant DNA from the strain.

By extracting an inserted DNA fragment from the obtained recombinant DNA and determining the nucleotide sequence of the fragment, the nucleotide sequence and the amino acid sequence of the DDPS gene or the DDPR gene and DDPS or DDPR can be determined.

Determination of nucleotide sequences, digestion and ligation of DNA, and so forth may be attained by those methods commonly used for gene cloning (detailed in, for example, Sambrook J., Fritsch, E. F. and Maniatis, T., 1989, Molecular Cloning: A Laboratory Manual, Second edition, Cold Spring Harbor Laboratory Press, Cold Spring Harbor, N.Y. etc.). They can also be conducted according to the instructions for each reagent, such as restriction enzymes and kits.

The DDPS gene of the present invention codes for DDPS that has the amino acid sequence of SEQ ID NO: 2. Specific examples of the DDPS gene of the present invention include DNA that has the nucleotide sequence of SEQ ID NO: 1. Furthermore, the DDPS gene of the present invention may have a nucleotide sequence which includes replacement of codons with equivalent codons, so long as the sequence codes for the same amino acid sequence as that shown as SEQ ID NO: 2.

Furthermore, the DDPS gene of the present invention may encode a protein which has the amino acid sequence of SEQ ID NO: 2, and includes substitution, deletion, insertion, addition, or inversion of one or several amino acids, or encode a protein which has DDPS activity. The term "several" amino acids as used herein means preferably 1–50 amino acids, more preferably 1–10 amino acids. Homology between the DDPS gene of the present invention and a known DDPS gene of *Bacillus subtilis* (*B. subtilis*) is 65.9% based on the nucleotide sequence, and 64.8% based on the encoded amino acid sequence.

The DDPR gene of the present invention codes for DDPR that has the amino acid sequence of SEQ ID NO: 4. Specific examples of the DDPR gene of the present invention include DNA that has the nucleotide sequence of SEQ ID NO: 3. Furthermore, the DDPR gene of the present invention may have a nucleotide sequence which includes replacement of codons with equivalent codons, so long as the sequence codes for the same amino acid sequence as that shown as SEQ ID NO: 4.

Furthermore, the DDPR gene of the present invention may encode for a protein which has an amino acid sequence of SEQ ID NO: 4, and includes substitution, deletion, insertion, addition, or inversion of one or several amino acids, or one coding for a protein which has DDPR activity. The term "several" amino acids used herein means preferably 140 amino acids, more preferably 1–10 amino acids. Homology between the DDPR gene of the present invention and a known DDPR gene of *Bacillus subtilis* (*B. subtilis*) is 66.7% based on the nucleotide sequence, and 67.5% based on the encoded amino acid sequence.

DNA that codes for the substantially same protein as DDPS or DDPR as described above is obtained by modifying the nucleotide sequence, for example, by means of the site-directed mutagenesis method so that one or more amino acid residues at a specific site contains a substitution, deletion, insertion, addition, or inversion. DNA modified as described above may also be obtained by conventionally known mutation treatments. Such mutation treatments include treating DNA encoding DDPS or DDPR in vitro, for example, with hydroxylamine or the like, and treating a microorganism, for example, a bacterium belonging to the genus *Escherichia*, harboring DNA encoding DDPS or DDPR with ultraviolet irradiation or a mutagenizing agent usually used for the mutation treatment such as N-methyl-N'-nitro-N-nitrosoguanidine (NTG) and nitrous acid.

The substitution, deletion, insertion, addition, or inversion of nucleotides as described above also includes mutation (mutant or variant) which naturally occurs, for example, due to the individual difference or the difference in species or genus of the microorganism that harbors DDPS or DDPR Such DNA coding for substantially the same protein as DDPS or DDPR is obtained by expressing DNA having mutation as described above in an appropriate cell, and investigating the DDPS or DDPR activity of the expression product DNA coding for substantially the same protein as DDPS or DDPR is also obtained by isolating DNA which is able to hybridize with a nucleotide sequence comprising the nucleotide sequence of SEQ ID NO: 1 or 3 or a part thereof, for example, a probe which can be prepared from the nucleotide sequence of SEQ ID NO: 1 or 3 by PCR, under stringent conditions, and codes for a protein having DDPS or DDPR activity.

The "stringent conditions" referred to herein are conditions under which a so-called specific hybrid is formed, and a non-specific hybrid is not formed. It is difficult to clearly define these conditions numerically. However, for example, stringent conditions include conditions under which DNA's having high homology, for example, DNA's having homology of not less than 40% are hybridized with each other, and DNAs having homology lower than the above are not hybridized with each other. Alternatively, stringent conditions are exemplified by conditions under which DNAs are hybridized with each other at a salt concentration corresponding to ordinary conditions of washing in Southern hybridization, i.e., 60° C., 1×SSC, 0.1% SDS, preferably 0.1×SSC, 0.1% SDS (see, for example, Sambrook, J., Fritsch, E. F. and Maniatis, T., Molecular Cloning: A Laboratory Manual, Second edition, 1989, Cold Spring Harbor Laboratory Press Cold Spring Harbor, N.Y. etc.).

Such genes which are able to hybridize under conditions as described above include those having a stop codon generated in the coding region of the genes, and those having no activity due to a mutation of the active center. However, such mutants can be easily removed by ligating the genes with a commercially available activity expression vector, and measuring the DDPS or DDPR activity. The DDPS activity can be measured by, for example, the method of Yugari et al. (Yugari Y. and Gilvarg C., *Journal of Biological Chemistry*, 240, 4710(1962)). Specifically, for example, the DDPS activity can be measured by allowing a reaction of 100 µl of 500 mM imidazole hydrochloride (pH 7.5), 100 µl of 20 mM aspartic acid semialdehyde (which can be synthesized by the method described in Black S. and Write N., *Journal of Biological Chemistry*, 213, 51 (1955)), 100 µl of 20 mM sodium pyruvate, and 100 µl of an enzyme solution in a total volume of 1 ml and measuring the increase in absorbance at 270 nm.

The DDPR activity can be measured by, for example, the method of Tamir et al. (Tamir H. and Gilvarg C., *Journal of Biological Chemistry*, 249, 3034(1974)). Specifically, for example, the DDPR activity can be measured by allowing a reaction of 100 µl of 500 mM imidazole hydrochloride (pH 7.5), 100 µl of dihydrodipicolinic acid, 100 µl of NADPH, and 100 μl of an enzyme solution in a total volume of 1 ml and measuring the decrease in absorbance at 340 nm.

Because the nucleotide sequences of the genes which code for DDPS and DDPR derived from *Bacillus methanolicus* have now been elucidated, the DNA sequence which codes for DDPS or DDPR can be obtained from a *Bacillus methanolicus* gene library by hybridization using an oligonucleotide probe based on each of the sequences. DNA sequences which code for the enzymes can also be obtained by amplification of the *Bacillus methanolicus* chromosomal DNA by PCR (polymerase chain reaction) using oligonucleotide primers based on the aforementioned nucleotide sequences.

<3> Application of DDPS Gene and DDPR Gene

The DDPS and DDPR genes of the present invention can be used for production of DDPS and DDPR. That is, DDPS can be produced by introducing DNA containing the DDPS gene into a suitable host cell, and culturing the obtained transformant to allow expression of the DNA. DDPR can be produced by introducing DNA containing the DDPR gene into a suitable host cell, and culturing the obtained transformant to allow expression of the DNA. The DDPS or DDPR protein can be collected from the culture and purified by known techniques, such as salting out, solvent precipitation, gel filtration chromatography, and ion exchange chromatography.

The DDPS and DDPR genes can also be utilized for breeding L-lysine producing bacteria. By introducing the DDPS gene, the DDPR gene, or both into a microorganism, L-lysine biosynthesis is enhanced and thus L-lysine producing ability is improved.

Examples of the host cell into which the DDPS gene or the DDPR gene is introduced include *Escherichia* bacteria, such as *Escherichia coli*, coryneform bacteria such as *Brevibacterium lactofermentum*, *Bacillus* bacteria such as *Bacillus methanolicus*, and so forth. Examples of the vector used for introducing the DDPS or DDPR gene into these hosts include, as for *Escherichia* bacteria, those mentioned above. As for coryneform bacteria, the following vectors are encompassed. The microorganisms which harbor each vector, and the accession numbers thereof at international depositories are shown in the parentheses, respectively.

pAJ655 *Escherichia coli* AJ11882 (FERM BP-136)
  *Corynebacterium glutamicum* SR8201 (ATCC39135)
pAJ1844 *Escherichia coli* AJ11883(FERM BP-137)
  *Corynebacterium glutamicum* SR8202 (ATCC39136)
pAJ611 *Escherichia coli* AJ11884 (FERM BP-138)
pAJ3148 *Corynebacterium glutamicum* SR8203 (ATCC39137)
pAJ440 *Bacillus subtilis* AJ11901 (FERM BP-140)

These vectors can be obtained from the deposited microorganisms as follows. Cells are collected at the logarithmic growth phase, and lysed with lysozyme and SDS to give a lysate, from which a supernatant solution is obtained by centrifugation at 30,000×g. Polyethylene glycol is added to the supernatant solution to perform fictional purification by means of cesium chloride-ethidium bromide equilibrium density gradient centrifugation.

To introduce a plasmid into *E. coli* to transform it, a method may be used in which recipient cells are treated with calcium chloride so as to increase the permeability of the cells for DNA (Mandel, M. and Higa, A., *J. Mol. Biol.*, 53, 159 (1970)) and so forth.

Examples of the vector for *Bacillus* bacteria include, for example, pUB110, pHY300PLK, pHV1248, pE194, pC194, pBC16, pSA0501, pSA2100, pAM77, pT181, pBD6, pBD8, pBD64, pHV14, and so forth.

Transformation of coryneform bacteria may be performed by the electric pulse method (Sugimoto et al., Japanese Patent Publication Laid-Open No. 2-207791/1990). Transformation of *Bacillus* bacteria may be performed by making host cells into the protoplast or spheroplast followed by introducing recombinant DNA into the DNA-recipient cells (Chang, S. and Choen, S. N., *Molec. Gen Genet.*, 168, 111 (1979); Bibb, M. J., Ward, J. M. and Hopwood, O. A., *Nature*, 274, 398 (1978); Hinnen, A, Hicks, J. B. and Fink, G. R., *Proc. Natl. Acad. Sci., USA*, 75, 1929 (1978)).

The DDPS or DDPR gene may be introduced into a host with a promoter proper for the gene, or the structural gene ligated to another promoter may be introduced. Examples of such a promoter include lac promoter, trp promoter, trc promoter, tac promoter, $P_R$ and $P_L$ promoter of λ phage, tet promoter, amyE promoter, spac promoter, and so forth L-lysine can be produced by culturing a microorganism which has been transformed with the DDPS or DDPR gene or both, and which has L-lysine producing ability in a medium, to produce and cause accumulation of L-lysine in the medium, and collecting the L-lysine from the medium.

Although medium and culture conditions can be suitably selected according to the host microorganism used, usual media which contains a nitrogen source, inorganic ions, and other organic trace amount nutrients as required can be used.

As the carbon source, saccharides such as glucose, lactose, galactose, fructose and hydrolysate of starch, alcohols such as glycerol and sorbitol, organic acids such as fumaric acid, citric acid and succinic acid, and so forth can be used.

When a methanol assimilating bacterium such as *Bacillus methanolicus* is used as the microorganism of the present invention, methanol is preferably used as the carbon source.

As the nitrogen source, inorganic ammonium salts such as ammonium sulfate, ammonium chloride and ammonium phosphate, organic nitrogen such as soybean hydrolysate, ammonia gas, aqueous ammonia and so forth can be used.

As the inorganic ions or sources thereof, a small amount of potassium phosphate, magnesium sulfate, iron ions, manganese ions, and so forth may be added. As a trace amount organic nutrient, it is desirable to add a suitable amount of required substances such as L-homoserine and vitamin $B_1$, yeast extract, and so forth as required.

The culture is performed under conditions suitable for growth of the chosen microorganism. In general, the culture is preferably performed for 16 to 72 hours under aerobic conditions, and the culture temperature is controlled at 20 to 45° C., and at pH 5–8.5 during the culture. To adjust the pH, inorganic or organic acidic or alkaline substances, ammonia gas, and so forth can be used. Furthermore, when a thermophilic bacterium is used as the host, it can be cultured at a temperate of 42 to 60° C.

Collection of L-lysine from the culture can usually be carried out by using a combination of known techniques, such as techniques using ion exchange resins, precipitation methods, and so forth.

EXAMPLES

Hereinafter, the present invention will be further specifically explained with reference to the following non-limiting examples.

The reagents used were obtained from Wako Pure Chemicals or Nakarai Tesque unless otherwise indicated. The composition of the media used in each example are shown below. All the media were subjected to steam sterilization at 120° C. for 20 minutes after the components were dissolved.

L Medium:

| Bacto trypton (DIFCO) | 1% |
|---|---|
| Yeast extract (DIFCO) | 0.5% |
| NaCl | 0.5% |

L Agar Medium:

| L medium | |
|---|---|
| Bacto agar (DIFCO) | 1.5% |

SOC Medium:

| Bacto trypton (DIFCO) | 2% |
|---|---|
| Yeast extract (DIFCO) | 0.5% |
| NaCl | 10 mM |
| KCl | 2.5 mM |
| $MgSO_4$ | 10 mM |
| $MgCl_2$ | 10 mM |
| Glucose | 20 mM |

Except for the magnesium solution and glucose, all the components were steam-sterilized, then 2 M magnesium stock solution (1 M $MgSO_4$, 1 M $MgCl_2$) and 2 M glucose solution which had been passed two times through a 0.22 μm filter were added.

TS Medium:

| Bacto trypton (DIFCO) | 1.5% |
|---|---|
| Bactosoyton (DIFCO) | 0.5% |
| NaCl | 0.5% |

TS Agar Medium:

| TS medium | |
|---|---|
| Bacto agar (DIFCO) | 1.5% |

M9 Minimal Medium:

| $Na_2HO_4.12H_2O$ | 8% |
|---|---|
| $KH_2PO_4$ | 1.5% |
| NaCl | 2.5% |
| $NH_4Cl$ | 0.5% |
| $MgSO_4.7H_2O$ | 246.48 mg/L |
| Glucose | 0.5% |
| pH 7.0 | |

$MgSO_4$ and glucose were separately sterilized and added. A suitable amount of amino acids and vitamins were added as required.

M9 Minimal Agar Medium:

| M9 minimal medium | |
|---|---|
| Bacto agar (DIFCO) | 1.5% |

Example 1

Cloning of the DDPS Gene from *Bacillus methanolicus* PB1 Strain

Preparation of Chromosomal DNA from *Bacillus methanolicus*

One loop of the *Bacillus methanolicus* PB1 strain (NCIMB13113) was inoculated into 5 ml of TS medium in a test tube, and cultured overnight at 50° C. with shaking. The culture was then inoculated into 50 ml of TS medium in a 500-ml volume Sakaguchi flask at a concentration of 1%, cultured at 50° C. for 56 hours, and the cells were collected by centrifugation. The cells were suspended in 50 ml of TEN solution (50 mM Tris-HCl (pH 8.0), 10 mM EDTA, 20 mM NaCl (pH 8.0)), collected by centrifugation, and suspended again in 5 ml of TEN solution containing 5 mg/ml of lysozyme and 10 μg/ml of ribonuclease A.

The suspension was maintained at 37° C. for 30 minutes, and then proteinase K and sodium laurylsulfate were added to final concentrations of 10 μg/ml and 0.5%, respectively. The suspension was maintained at 70° C. for 2 hours, then an equal volume of a saturated phenol solution (phenol solution saturated with 10 mM Tris-HCl (pH 8.0)) was added, and centrifuged. The supernatant was collected, and mixed with an equal volume of a phenol/chloroform solution (phenol:chloroform:isoamyl alcohol=25:24:1), and centrifuged.

The supernatant was collected, and the same procedure as above was repeated by adding an equal volume of a chloroform solution (chloroform:isoamyl alcohol=24:1). The supernatant was mixed with 1/10 volume of 3 M sodium acetate (pH 4.8) and 2.5-fold volume of ethanol to precipitate the chromosomal DNA. The precipitate was collected by centrifugation, washed with 70% ethanol, dried under vacuum, and dissolved in an appropriate amount of TE solution (10 mM Tris-HCl, 1 mM EDTA (pH 8.0)).

Ligation of Vector DNA and Chromosomal DNA

50 μl of the chromosomal DNA (1 μg/μl) obtained in (1), 20 μl of H buffer (500 mM Tris-HCl, 100 mM $MgCl_2$, 10 mM dithiothreitol, 1000 mM NaCl (pH 7.5)), and 8 units of restriction enzyme Sau3AI (Takara Shuzo) were allowed to react in a total volume of 200 μl at 37° C. for 10 minutes, and then the reaction mixture was mixed with 200 μl of the phenol/chloroform solution to stop the reaction.

The mixture was centrifuged to obtain an upper layer, which was separated on a 0.8% agarose gel. A DNA fragment corresponding to 2–8 kilobase pairs (hereinafter "kbp") was collected from the gel using EASYTRAP (glass powder for collection of DNA, produced by Takara Shuzo) to obtain 50 μl of a fractionated DNA solution.

Separately, 5 μl of 0.5 μg/μl plasmid pSTV28 (produced by Takara Shuzo), 2 μl of K buffer (200 mM Tris-HCl, 100 mM $MgCl_2$, 10 mM dithiothreitol, 1000 mM KCl (pH 8.5)) and 10 units of restriction enzyme BamHI (produced by Takara Shuzo) were allowed to react in a total volume of 20 μl at 37° C. for 2 hours, then 20 units of calf small intestine alkaline phosphatase produced by Takara Shuzo) was added, and allowed to react for an additional 30 minutes. The reaction mixture was mixed with an equal volume of the phenol/chloroform solution, and centrifuged. The supernatant was collected, and the same procedure as above was repeated by adding an equal volume of the chloroform solution. 1/10 volume of 3 M sodium acetate (pH 4.8) and 2.5-fold volume of ethanol was added to the supernatant to precipitate the DNA. The precipitate was collected by centrifugation, washed with 70% ethanol, dried under vacuum, and dissolved in TE solution.

The Sau3AI digest of the chromosomal DNA fractionated in (1) and the BamHI digest of pSTV28 were ligated using Ligation Kit ver. 2 (Takara Shuzo). 1/10 volume of 3 M sodium acetate (pH 4.8) and 2.5-fold volume of ethanol were added to the ligation reaction mixture to precipitate the DNA. The precipitate was collected by centrifugation, washed with 70% ethanol, dried under vacuum, and dissolved in TE solution.

Preparation of Gene Library

One loop of *Escherichia coli* JM109 was inoculated into 5 ml of L medium contained in a test tube, and cultured overnight at 37° C. with shaking. The culture was then inoculated into 50 ml of L medium in a 500-ml volume Sakaguchi flask at a concentration of 1%, and cultured at 37° C. until $OD_{660}$ reached 0.5–0.6. The culture was cooled on ice for 15 minutes, and centrifuged at 4° C. to collect the cells. The cells were washed by suspending them in 50 ml of ice-cooled water and subjecting the suspension to centrifugation. This procedure was repeated once again, and the cells were washed by suspending them in 50 ml of 10% glycerol solution cooled with ice and subjecting the suspension to centrifugation. The cells were suspended in an equal volume of 10% glycerol solution, and divided into portions of 50 μl volume. To 50 μl of the cell mixture, 1 μl of the ligation solution as prepared above was added, and the mixture was transferred to a cuvette (for exclusive use in an electoporation apparatus of BioRad Co., width of 0.1 cm) and cooled with ice beforehand. Conditions of the electoporation apparatus were set at 1.8 kV and 25 μF, and the pulse controller was set at 200 ohms. The cuvette was mounted on the apparatus and pulse was applied. After the application of the pulse, 0.5 ml of SOC medium was immediately added to the mixture, transferred to a sterilized test tube, and cultured at 37° C. for 1 hour with shaking. The culture was plated on L agar medium containing 20 μg/ml of chloramphenicol, and incubated overnight at 37° C.

The colonies which emerged were collected by scraping, inoculated into 50 ml of L medium in a 500-ml volume Sakaguchi flask, and cultured at 37° C. for 2 hours with shaking. Plasmid DNA was extracted from the cultured cells by the alkali SDS method to obtain a gene library solution.

Isolation of Clone with the DDPS Gene

The *Escherichia coli* AT998 strain deficient in the DDPS gene (CGSC 4548) was transformed with the aforementioned gene library solution by electroporation as described above. After application of pulse, SOC medium was added to the transformation solution, and the cells were cultured at 37° C. with shaking. The culture was centrifuged, and the cells were washed by suspending them in 5 ml of sterilized water and centrifuging the suspension. This washing procedure was repeated once again, and the cells were suspended in 500 μl of sterilize water. The suspension was plated on M9 minimal agar medium containing 20 μg/ml of chloramphenicol, and incubated at 37° C. for 2–3 days. Because the *Escherichia coli* M998 strain is deficient in the DDPS gene, it cannot grow on M9 minimal medium which does not contain diaminopimelic acid. However, a transformant strain thereof which contains the DDPS gene derived from *Bacillus methanolicus* can grow on M9 minimal medium due to the functional gene.

The recombinant vector was extracted from the colonies which emerged, and the inserted fragment was confirmed. A transformant with the vector pSTV28 could not grow on M9 minimal medium, whereas the *Escherichia coli* AT998 stain transformed with the above recombinant plasmid grew on M9 minimal medium. Thus, it was confirmed that the obtained insert contained the DDPS gene.

The *Escherichia coli* AT998 strain which harbors the plasmid containing the DDPS gene obtained as described above was designated *Escherichia coli* AJ13633. The AJ13633 strain was deposited at National Institute of Bioscience and Human-Technology, Agency of Industrial Science and Technology, Ministry of International Trade and Industry (postal code 305-8566, 1-3 Higashi 1-chrome, Tsukuba-shi Ibaraki-ken, Japan) on Jul. 26, 1999 and granted an accession number of FERM P-17485, and converted to an international deposit in accordance with the Budapest Treaty on Jul. 14, 2000, and granted number FERM BP-7221.

Determination of the Nucleotide Sequence of the DDPS Gene

A plasmid containing the DDPS gene was prepared from *Escherichia coli* AJ13633, and the nucleotide sequence of the DDPS gene derived from *Bacillus methanolicus* PB1 was determined by the dideoxy method. The coding region of the determined nucleotide sequence of the DDPS gene is shown as SEQ ID NO: 1. The amino acid sequence encoded by the nucleotide sequence is shown as SEQ ID NO: 2. Nucleotide and amino acid sequences were analyzed with the Genetyx-Mac computer program (Software Development Co., Tokyo, Japan). The homology analysis was carried out according to the method developed by Lipman and Peason (*Science*, 227, 1435–1441, 1985). As a result of the homology search, and since this amino acid sequence shows a high homology of 64.8% to DDPS derived from *Bacillus subtilis*, the obtained gene was identified as the DDPS gene derived from *Bacillus methanolicus*.

Example 2

Cloning of the DDPR Gene from *Bacillus methanolicus* PB1 Strain

Isolation of Clone with the DDPR Gene

The *Escherichia coli* AT999 strain deficient in the DDPR gene (CGSC4549) was transformed with a gene library solution prepared in the same manner as Example 1(3) by electroporation as described above. After the pulse was applied, SOC medium was added to the transformation solution, and the cells were cultured at 37° C. with shaking. Then, the culture was plated on L agar medium containing 20 μg/ml of chloramphenicol, and incubated at 37° C. overnight. Since the *Escherichia coli* AT999 stain is deficient in the DDPR gene, its growth was very slow in L medium that does not contain diaminopimelic acid. However, a transformant strain that contains the DDPR gene derived from *Bacillus methanolicus* shows normal growth even on L medium, since the gene is functional. Furthermore, the AT999 strain cannot grow on M9 minimal medium, whereas a transformant stain thereof that contains the DDPR gene derived from *Bacillus methanolicus* can grow on M9 minimal medium, since the gene is functional.

A colony normally grown on L medium was cultured on M9 agar medium as streak culture to confirm that the DDPR gene was functioning in the transformant strain. Plasmid was extracted from colonies which emerged on M9 medium, and an insert was confirmed. A transformant with vector pSTV28 could not grow on M9 minimal medium, whereas the *Escherichia coli* AT998 strain transformed with the above recombinant plasmid grew on M9 minimal medium. Thus, it was confirmed that the obtained insert contained the DDPR gene.

The *Escherichia coli* AT999 strain which harbors the plasmid containing the DDPR gene obtained as described above was designated *Escherichia coli* AJ13634. The AJ13634 strain was deposited at National Institute of Bioscience and Human-Technology, Agency of Industrial Science and Technology, Ministry of International Trade and Industry (postal code 305-8566, 1-3 Higashi 1-chrome, Tsukuba-shi Ibaraki-ken, Japan) on Jul. 26, 1999 and granted an accession number of FERM P-17486, and converted to an international deposit in accordance with the Budapest Treaty on Jul. 14, 2000, and granted number FERM BP-7222.

(2) Determination of the Nucleotide Sequence of the DDPR Gene

A plasmid containing the DDPR gene was prepared from *Escherichia coli* AJ13634, and the nucleotide sequence of the DDPR gene derived from *Bacillus methanolicus* PB1 was determined by the dideoxy method. The coding region of the determined nucleotide sequence of the DDPS gene is shown as SEQ ID NO: 3. The amino acid sequence encoded by the nucleotide sequence is shown as SEQ ID NO: 4. Nucleotide and amino acid sequence were analyzed with the Genetyx-Mac computer program (Software Development Co., Tokyo, Japan). The homology analysis was carried out according to the method developed by Lipman and Peason (*Science*, 227, 1435–1441, 1985). As a result of the homology search, and since this amino acid sequence shows a high homology of 67.5% to DDPR derived from *Bacillus subtilis*, the obtained gene was identified as the DDPR gene derived from *Bacillus methanolicus*.

While the invention has been described in detail with reference to preferred embodiments thereof it will be apparent to one skilled in the art that various changes can be made, and equivalents employed, without departing from the scope of the invention. Each of the aforementioned documents is incorporated by reference herein in its entirety, including the foreign priority document 11-221468 filed in Japan on Aug. 4, 1999.

What is claimed is:

1. An isolated DNA which hybridizes under stringent conditions to nucleotides 1 to 798 in SEQ ID NO: 3, wherein said stringent conditions comprise washing in 0.1×SSC and 0.1% SDS at 60° C., and wherein said DNA codes for a protein which has dihydrodipicolinate reductase activity.

2. A microorganism which is transformed with the DNA according to claim 1 in a form that allows expression of a protein encoded by said DNA.

3. An isolated DNA which codes for a protein having the amino acid sequence of SEQ ID NO: 4.

4. The DNA according to claim 3, comprising the nucleotide sequence of nucleotides 1 to 798 in SEQ ID NO: 3.

5. A microorganism which is transformed with the DNA according to claim 4 in a form that allows expression of a protein encoded by said DNA.

6. A microorganism which is transformed with the DNA according to claim 3 in a form that allows expression of a protein encoded by said DNA.

7. An isolated DNA which codes for a protein comprising the amino acid sequence of SEQ ID NO: 4, which includes substitutions, deletions, insertions, additions, or inversions of 1–10 amino acids, and wherein said protein has dihydrodipicolinate reductase activity.

8. A microorganism which is transformed with the DNA according to claim 7 in a form that allows expression of a protein encoded by said DNA.

9. A method for producing L-lysine comprising culturing the microorganism according to claim 8 in a medium, and collecting the L-lysine from said medium.

10. A method for producing L-lysine comprising culturing the microorganism according to claim 2 in a medium, and collecting the L-lysine from said medium.

11. A method for producing L-lysine comprising culturing the microorganism according to claim 6 in a medium, and collecting the L-lysine from said medium.

12. A method for producing L-lysine comprising culturing the microorganism according to claim 5 in a medium, and collecting the L-lysine from said medium.

* * * * *